United States Patent
Hafemann

(10) Patent No.: US 6,701,565 B2
(45) Date of Patent: Mar. 9, 2004

(54) ELECTRIC TOOTHBRUSH WITH REVOLVABLE BRUSH HEAD

(75) Inventor: Klaus Hafemann, Essen (DE)

(73) Assignee: Wik Far East Ltd., North Point (CN)

( * ) Notice: Subject to any disclaimer, the term of this patent is extended or adjusted under 35 U.S.C. 154(b) by 323 days.

(21) Appl. No.: 09/846,204

(22) Filed: Apr. 30, 2001

(65) Prior Publication Data

US 2002/0157197 A1 Oct. 31, 2002

(51) Int. Cl.[7] .............................. A46B 13/00; A46B 7/06
(52) U.S. Cl. ........................................ 15/22.1; 15/22.2
(58) Field of Search ................. 15/22.1, 22.2, 15/28

(56) References Cited

U.S. PATENT DOCUMENTS

| 3,233,265 A | * | 2/1966 | Hartmann | 15/22.1 |
| 3,935,869 A | * | 2/1976 | Reinsch | 132/271 |
| 4,336,622 A | * | 6/1982 | Teague et al. | 15/22.1 |
| 5,259,083 A | | 11/1993 | Stansbury, Jr. | 15/22.1 |
| 5,504,958 A | * | 4/1996 | Herzog | 15/22.1 |
| 6,453,498 B1 | * | 9/2002 | Wu | 15/22.1 |
| 6,574,820 B1 | * | 6/2003 | DePuydt et al. | 15/28 |
| 2003/0084524 A1 | * | 5/2003 | Blaustein et al. | 15/22.1 |

FOREIGN PATENT DOCUMENTS

| DE | 3505897 | 8/1986 |
| DE | 4343103 | 6/1995 |
| DE | 19627752 | 1/1998 |
| WO | WO99/12492 | 3/1999 |

* cited by examiner

Primary Examiner—Robert J. Warden, Sr.
Assistant Examiner—Laura C Cole
(74) Attorney, Agent, or Firm—Flanagan & Flanagan; John R. Flanagan

(57) ABSTRACT

An electric toothbrush includes a handle, a brush head defining a brushing plane, and a guide arrangement supported by the handle and, in turn, supporting the brush head to undergo movement along an endless path of revolution having an axis extending substantially parallel to the brushing plane such that the brushing plane is maintained in the same orientation relative to a surface of a set of teeth throughout movement of the brush head along the endless path of revolution.

8 Claims, 3 Drawing Sheets

ELECTRIC TOOTHBRUSH WITH REVOLVABLE BRUSH HEAD

BACKGROUND OF THE INVENTION

1. Field of the Invention

The present invention relates to electric toothbrushes and, more particularly, is concerned with a brush head on an electric toothbrush defining a brushing plane and being supported for movement along a path of revolution having an axis extending substantially parallel to the brushing plane such that the brushing plane is maintained in the same orientation relative to a set of teeth throughout movement of the brush head along the path of revolution.

2. Description of the Prior Art

Known prior art electric toothbrushes typically include a handle, a drive unit mounted in the handle and having a drive shaft extending to an end of the handle, and a brush head rotatably supported at the end of the handle and driven via a driving linkage to the drive shaft such that a cleaning or brushing plane formed by ends of bristles of the brush head is set to undergo a rotary turning motion for cleaning a set of teeth. The typical drive unit in the handle includes an electric motor and a battery providing a source of voltage to operate the electric motor. If appropriate, the battery can be of the rechargeable type. Also, electrical switches can be provided on the handle and connected in a circuit with the electric motor and battery for switching the motor on and off.

In these known prior art electric toothbrushes, the brush head is supported for undergoing rotation about an axis extending perpendicular to the cleaning or brushing plane of the brush head. In some of these prior art electric toothbrushes, the brush head is setup to undergo an oscillatory turning motion in which the brush head swivels in one direction through a preset angle, for example of seventy degrees, and subsequently through the same preset angle in the opposite direction. In other of these prior art electric toothbrushes, the brush head is setup to undergo continuous rotation in one direction about its rotational axis extending at a right angle to the brushing plane of the brush head. A common feature of both types of brush head movements is that the bristles of the brush head are moved unevenly, since the inner bristles located adjacent to the rotational axis travel only a small distance during the turning motion of the brush head whereas the outer bristles located remote from the rotational axis travel a much greater distance. The cleaning effect of such a rotary brush head is therefore considerably greater with the bristles in its outer region than with the bristles in its inner region. In order to attain a substantially uniform cleaning effect over the entire tooth surface, the toothbrush must be moved as evenly as possible over the teeth.

In the case of toothbrushes whose brush head is driven to exert the oscillatory turning motion, the efficiency of the energy made available by the battery is lower than in such toothbrushes whose brush head carries out a rotary turning motion since, due to the reversal of the regular movement, dead points at the opposite ends of the oscillatory path must be overcome which is energy consuming.

However, in providing an electric toothbrush with a brush head which carries out a continuous rotary turning motion about a rotational axis perpendicular to the brushing plane, due to the evenness of the rotary movement the particles to be removed from the set of teeth can only be carried away with difficulty. Rather, such particles, for example food particles, press into the bristles of the brush head. In the case of the brush heads with oscillatory turning motion, through the continuous back and forth rotation of the brush head such particles can be spun or rinsed away.

Consequently, a need exists to provide an innovation in an electric toothbrush that will overcome these problems in prior art electric toothbrushes without introducing new problems in place thereof.

SUMMARY OF THE INVENTION

The present invention overcomes the aforementioned problems by providing an electric toothbrush which includes a handle, a brush head defining a brushing plane, and a guide arrangement supported by the handle and, in turn, supporting the brush head to undergo movement along an endless path of revolution having an axis of revolution extending substantially parallel to the brushing plane such that the brushing plane is maintained in the same orientation relative to a surface of a set of teeth throughout movement of the brush head along the endless path of revolution. Such brush head so provided on an electric toothbrush ensures a highly efficient utilization of the available electrical energy as well as the attainment of a more even and thus improved brushing result.

In contrast to the prior art, the brush head of the electric toothbrush of the present invention is not supported such that the brushing plane of the bristle ends remains unchanged but rather is supported such that the brush head, when driven, carries out a revolving motion in which the brushing plane with respect to its orientation relative to the surface of the teeth remains substantially unchanged. Because of the revolving motion of the brush head, all bristles of the brush head are moved evenly along the surface of the teeth to be cleaned which has not only an advantageous effect of even wear of the individual bristles but also of an even brushing.

Also through the revolving movement of the brush head and corresponding displacement of the brushing plane of the bristle ends along the endless path of revolution, the brush head, during operation of the electric toothbrush, is lifted with each revolving movement off the surface of the teeth, applied again at another site on the surface of the teeth, moved along the surface of the teeth and again lifted. This entails the advantages that a brushing movement is possible in a substantially linear direction and that through the lifting of the brush head dissolved or loosened food particles can be flushed away from the brush head by the foam of a tooth cleaning means. This cleaning or brushing movement is usefully provided, or is presettable by adjusting the direction of revolving movement of the brush head, such that the brush head is moved away from the gum tissue independently of the orientation of the toothbrush. Tooth brushing with a brush head moved in this way is especially gentle on the gum tissue.

By carrying out the revolving of the brush head in a continuous motion in one direction, the energy efficiency of an available voltage source is increased since, in contrast to brush heads with an oscillatory turning motion, no dead points need to be overcome. Consequently, the driving force is also greater such that to generate the same force a less powerful electric motor can also be used. However, in accordance with the present invention, the brush head can also usefully be provided so to additionally carry out an oscillating movement.

In one exemplary embodiment, the brush head is usefully driven by a rotary crank drive wherein the brush head itself is supported by a reciprocatory guide arrangement such that, upon being driven, the brush head carries out the desired revolving motion. A switch can be usefully disposed in the handle such that the brush head can be driven in the one as well as also in the opposite direction.

These and other features and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

In the following detailed description, reference will be made to the attached drawings in which.

DETAILED DESCRIPTION OF THE INVENTION

Figure 1:
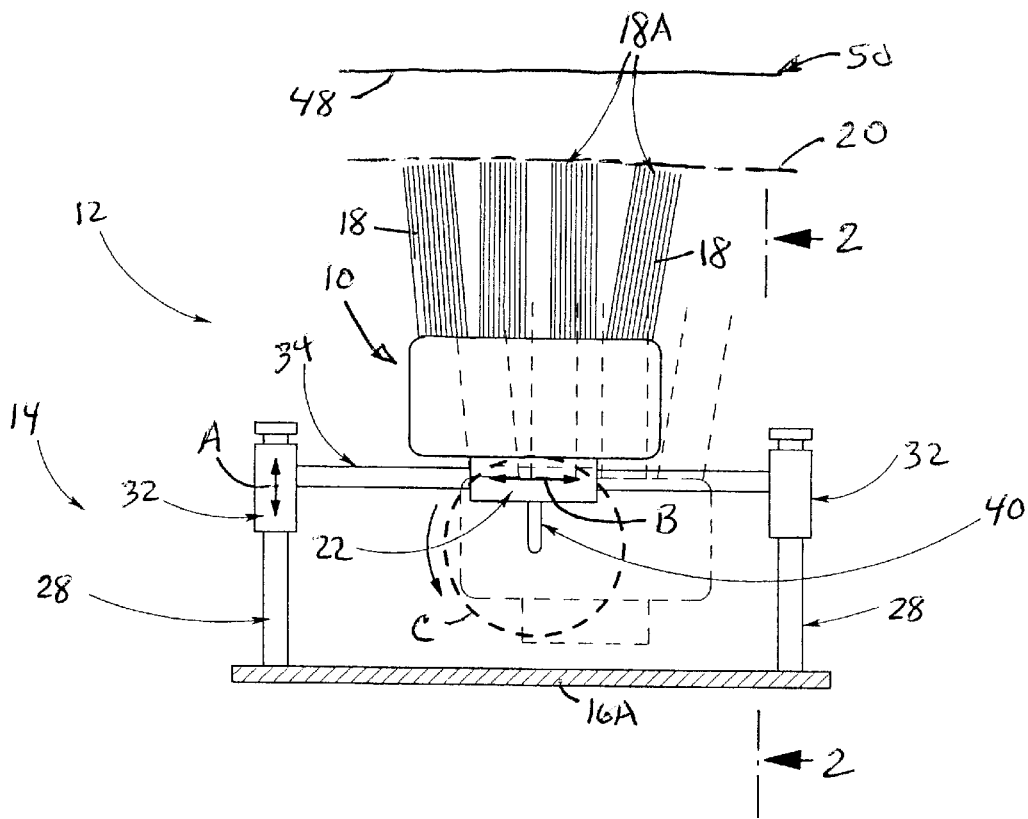
FIG. 1 is a schematic end elevational representation of a brush head of an electric toothbrush according to a first exemplary embodiment of the present invention.
Figure 2:
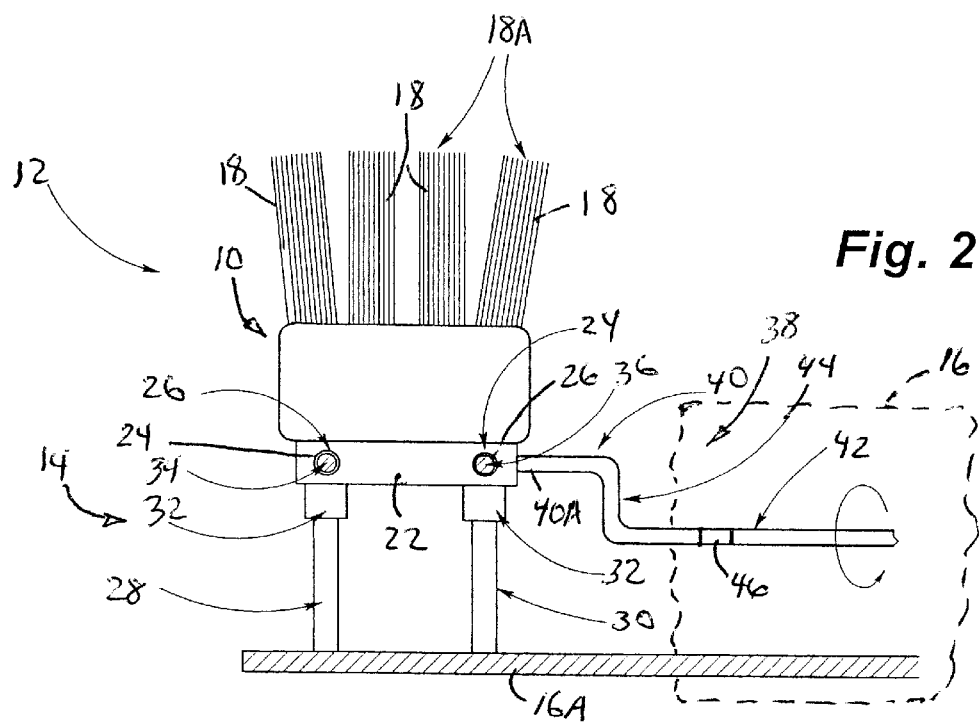
FIG. 2 is a schematic side representation of the brush head taken along line 2—2 of FIG. 1.

Referring to the drawings and particularly to FIGS. 1 and 2, there is illustrated a schematic representation of a brush head of an electric toothbrush, generally designated 12, according to a first exemplary embodiment of the present invention. The brush head 10 is supported by a guide arrangement 14 of the electric toothbrush 12 which, in turn, is supported at an end of a handle 16 of the electric toothbrush 12 on a forwardly extending portion 16A thereof. The brush head 10 carries a number of bristle tufts or bristles 18 whose upper terminal ends 18A define a cleaning or brushing plane 20. At an underside thereof, the brush head 10 includes a base plate 22 having forward and rearward spaced apart bores 24 extending parallel to one another through the plate 22 and between opposite sides 22A thereof and liners 26 extending through and set within the bores 24 of the plate 22.

The guide arrangement 14 of the electric toothbrush includes forward and rearward spaced apart pairs of guide posts 28, 30 (only three of the four guide posts being seen in FIGS. 1 and 2) fixed upright on the handle portion 16A, extending parallel with respect to one another and displaced from the opposite sides 22A of the plate 22. The guide arrangement 14 also includes a plurality of tubular sleeves 32 each received over one of the upright guide posts 28, 30 for undergoing slidably displaceable movement therealong in the vertical direction, as indicated by a double arrow A in FIG. 1. The guide arrangement 14 further includes forward and rearward spaced apart elongated slide rods 34, 36 attached at opposite ends to the sleeves 32 and extending perpendicular relative to the guide posts 28, 30 and sleeves 32 through the liners 26 in the corresponding forward and rearward spaced apart bores 24 through the plate 22. The slide rods 34, 36 thus extend parallel to one another in a common plane and transversely to the guide posts 28, 30 and sleeves 32, carry the plate 22 and thus the brush head 10 therewith vertically with movement of the sleeves 32 vertically along the guide posts 28, 30 and guide movement of the plate 22 and the brush head 10 therewith horizontally along the slide rods 34, 36, as indicated by the other double arrow B in FIG. 1. Only the forward slide rod 34 is seen in FIG. 1, whereas both forward and rearward slide rods 34, 36 are evident in FIG. 1.

The electric toothbrush 12 further includes a drive mechanism 38 in the form of a rotary crank 40 and a drive shaft 42 of an electric motor (not shown) disposed in the handle 16 of the electric toothbrush which rotatably drives the rotary crank 40. The rotary crank 40 has a shaft 44 drivingly connected by a coupling 46 to the drive shaft 42 and an output end 40A rotatably connected to the plate 22 of the brush head 10. Upon the rotary crank 40 being rotatably driven by the drive shaft 42, the plate 22 and thus the brush head 10 are revolved about an endless path of revolution C, as indicated by the continuous dashed line in FIG. 1, preferably of a circular configuration. Through the vertical guidance of the forward and rearward guide posts 28, 30 of the guide arrangement 14 and the mounting to and horizontal guidance of the slide rods 34, 36 of the guide arrangement 14, the rotation of the crank 40 in either direction caused revolving movement of the plate 22 and brush head 10 therewith along the endless path of revolution C such that the orientation of the brush head 10 as well as the brushing plane 20, as shown in FIG. 1, remain unchanged relative to a surface 48 of a set of teeth 50 such that the brushing plane 20 also carries out such revolving movement without the brush head 10 tilting. The result is that the teeth 50 are thoroughly cleaned by the bristles 18.

Furthermore, such support by the guide arrangement 14 of the brush head 10 via the plate 22 allows the brush head 10 to be reversibly drivable such that, as a function of the position of the brush head 10 with respect to gum tissue, in any event a cleaning movement away from the gum tissue can be carried out. All bristles 18 of the brush head 10 are moved evenly past the surface 48 of the teeth 50 such that, unlike with the prior art, an even cleaning effect is attained in the entire cleaning or brushing plane 20 of the bristle ends 18A.

Figure 3:
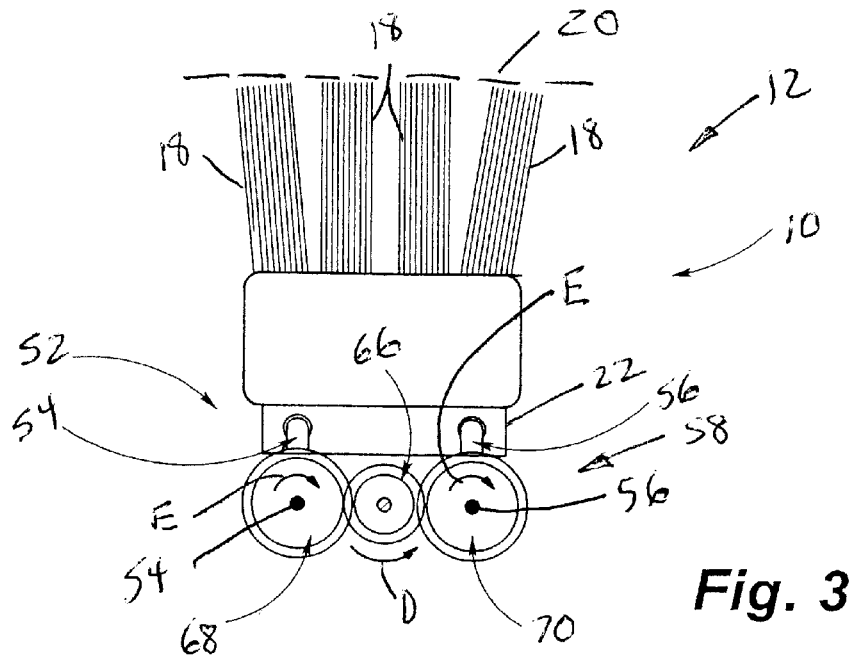
FIG. 3 is a schematic end elevational representation of a brush head of an electric toothbrush according to a second exemplary embodiment of the present invention.
Figure 4:
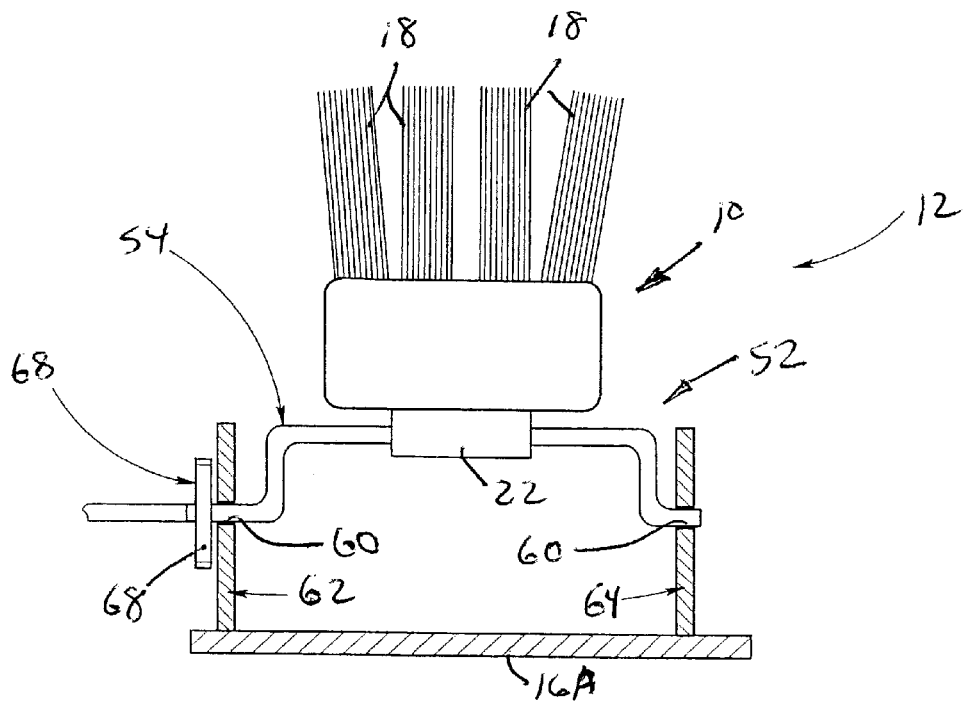
FIG. 4 is a schematic side representation of the brush head of FIG. 3.

Referring now to FIGS. 3 and 4, there is illustrated a schematic representation of the brush head 10 of the electric toothbrush 12 according to a second exemplary embodiment of the present invention. In this embodiment, the brush head 10 is supported on a two-throw crank guide arrangement 52 which includes two individual cranks 54, 56 spaced apart forwardly and rearwardly of one another. The brush head 10 is driven by a drive mechanism 58 which equally rotatably drives the cranks 54, 56 such that the brush head 10 carries out a revolving movement corresponding to that in the first embodiment of FIG. 1. The cranks 54, 56 are rotatably supported through holes 60 in a pair of laterally spaced walls 62, 64 of the guide arrangement 52 fixed upright on the handle portion 16A. The drive mechanism 58 includes a middle drive gear wheel 66 which is fixedly mounted on an output end 42A of the drive shaft 42 extending from the electric motor in the handle 16 and two equal driven gear wheels 68, 70 fixedly mounted on the cranks 54, 56 and disposed on opposite sides of the middle drive gear wheel 66 and drivingly coupled therewith. Upon the rotation of the middle drive gear wheel 66 by the drive shaft 42 in the direction indicated by the arrow D in FIG. 3, the driven gear wheels 68, 70 are set into an equal rotary turning motion, as indicated by the arrows E in FIG. 3, such that the cranks 54, 56 cause the brush head 10 to carry out the revolving motion corresponding to that carried out in the first embodiment in FIG. 1.

Figure 5:
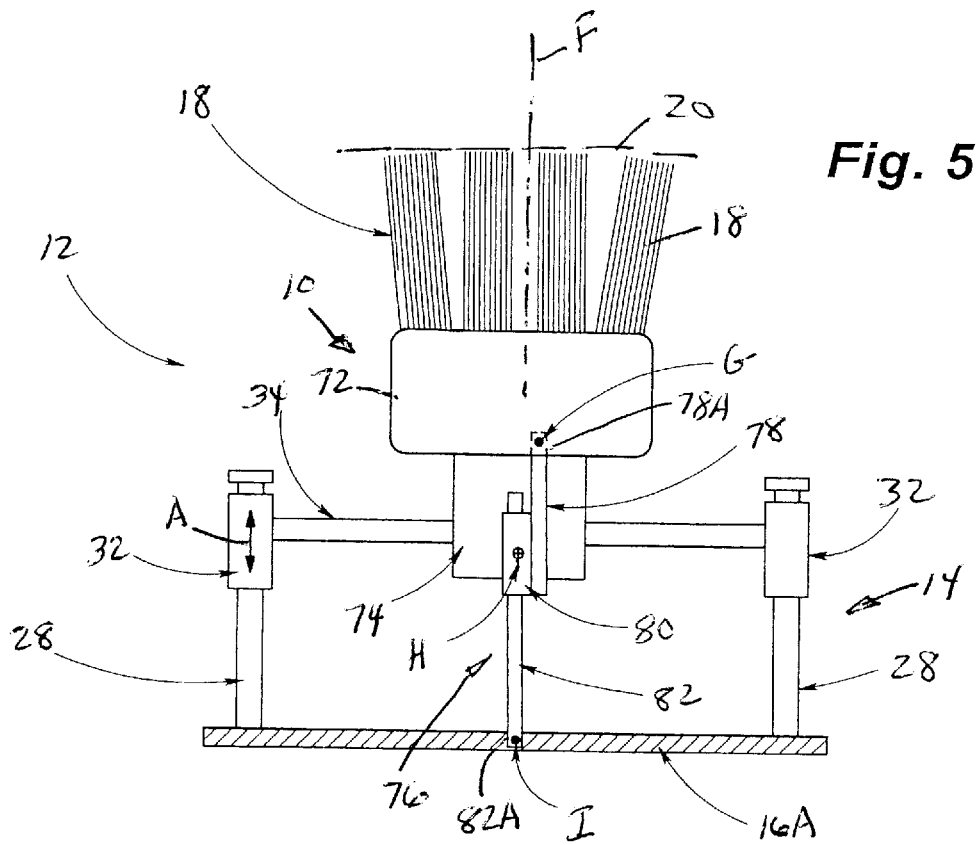
FIG. 5 is a schematic end representation of a brush head of an electric toothbrush according to a third exemplary embodiment of the present invention, showing the brush head in a first position of movement.
Figure 6:
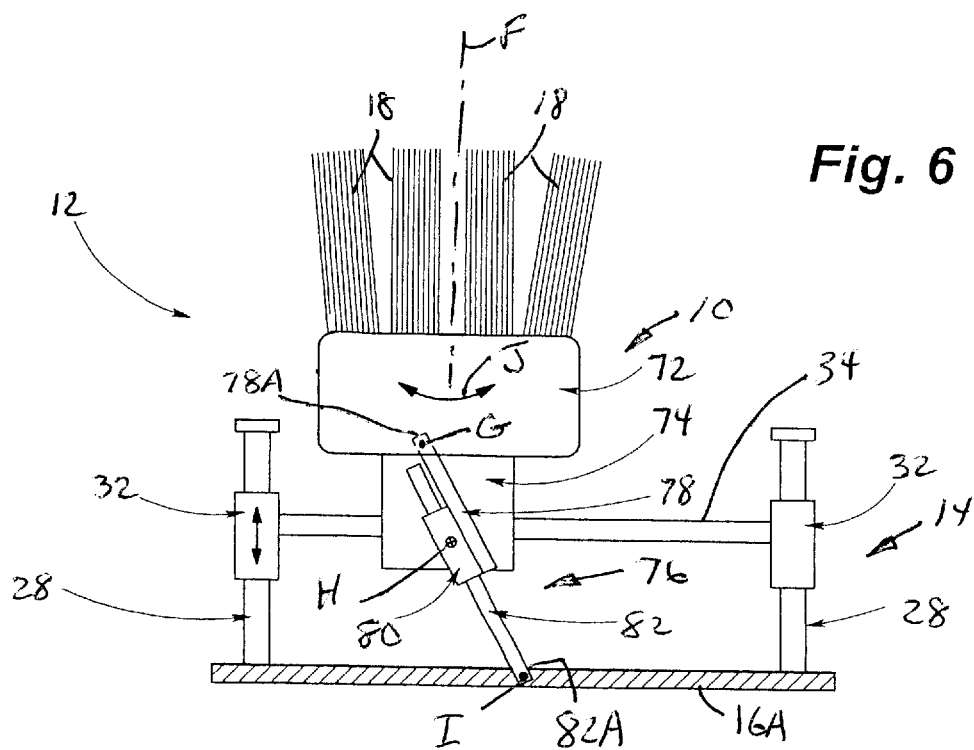
FIG. 6 is a schematic end representation similar to that of FIG. 5, now showing the brush head in a further position of movement.

Referring now to FIGS. 5 and 6, there is illustrated a schematic representation of the brush head 10 of the electric toothbrush 12 according to a third exemplary embodiment of the present invention. The brush head 10 is supported in a movable guide arrangement 14 being the same as in the first embodiment in FIG. 1. Thus, the components of the guide arrangement 14 in FIGS. 5 and 6 are denoted with the same reference numerals as in FIG. 1. The brush head 10 is also driven by a rotary crank (not shown) along the endless path of revolution the same as in the first embodiment in FIG. 1. However, different from the first embodiment in FIG. 1, the brush head 10 in the third embodiment of FIGS. 5 and 6 has a head portion 72 on which the bristles 18 are mounted and a base or plate portion 74 which supports the head portion 72 to undergo rotation relative to the plate portion 74 about a vertical rotational axis F, while at the same time undergoing revolving movement with the plate portion 74 along the endless path of revolution the same as the brush head 10 with the plate 22 in FIG. 1.

The electric toothbrush 12 of the third embodiment further includes a linkage 76 movably interconnecting the head portion 72 of the brush head 10, the plate portion 74 of the brush head 10 and the handle portion 16A of the handle 16. The linkage 76 includes a first link rod 78, a tubular casing 80 fixed along a side of the first link rod 78, and a second link rod 82 slidably extending into the tubular casing 80. The first link rod 78 at an upper end 78A thereof is articulately connected to a side of the head portion 72 of the brush head 10 such that the first link rod 78 can undergo pivotal movement relative to the head portion 72 of the brush head 10 about an upper horizontal rotational axis G. The tubular casing 80 on the first link rod 78 is articulately connected to the plate portion 74 of the brush head 10 such that the tubular casing 80 and the first link rod 78 together can undergo pivotal movement relative to the plate portion 74 about a middle horizontal rotational axis H. In order to permit a rotational turning motion of the head portion 72 of the brush head 10 relative to the plate portion 74 thereof about the vertical rotational axis F, the first link rod 78 is connected to the head portion 72 of the brush head 10 with sufficient play in the vertical direction at the upper rotational axis G. The second link rod 82 at a lower end 82A thereof is articulately connected to the handle portion 14A such that the second link rod 82 can undergo pivotal movement relative to the handle portion 16A about a lower horizontal rotational axis I. The sliding movement of the second link rod 82 relative to the casing 80 on the first link rod 78 together with the overall pivotal movement of the linkage 76 about the respective axes G, H, I accommodate both vertical and horizontal components of the revolving movement of the brush head 10 about the endless path of revolution. The horizontal component of the revolving movement of the plate portion 74 of the brush head 10 also causes pivoting of the linkage 76 about the respective axes G, H, I and translatory movement of the second link rod 82 relative to the casing 80 and first link rod 78 such that the head portion 72 of the brush head 10 also is caused to rotate about the vertical axis F in an oscillatory manner along a predetermined angular path, as indicated by the double arrow J in FIG. 6, relative to the plate portion 74 of the brush head 10 as both the head and plate portions 72, 74 of the brush head 10 move together along the endless path of revolution. Thus, the head portion 72 of the brush head 10 during an operation of the electric toothbrush is additionally set into an oscillating movement as represented by the double arrow J in FIG. 6.

In conclusion, based on the foregoing description of the electric toothbrush, it is evident that with the electric toothbrush 12 an especially effective cleaning action can be attained by the revolving motion of the brush head 10. The revolving motion of the brush head 10 also has an advantageous effect on the self-cleaning of the brush head 10 if used properly. The revolving motion of the brush head 10 can further be utilized to enable the carrying out an effective gum tissue massage with the electric toothbrush.

It is thought that the present invention and its advantages will be understood from the foregoing description and it will be apparent that various changes may be made thereto without departing from the spirit and scope of the invention or sacrificing all of its material advantages, the form hereinbefore described being merely preferred or exemplary embodiment thereof.

I claim:

1. An electric toothbrush, comprising:

(a) a handle;

(b) a brush head defining a brushing plane; and (c) a guide arrangement supported on said handle and, in turn, supporting said brush head to undergo movement along an endless path of revolution having an axis of revolution extending substantially parallel to said brushing plane of said brush head such that said brushing plane is maintained in a given orientation relative to a surface of a set of teeth throughout movement of said brush head along the endless path of revolution, said guide arrangement including (i) forward and rearward pairs of upright guide posts spaced apart and extending parallel to one another, and (ii) a plurality of sleeves each mounted over and slidable along one of said guide posts.

2. The toothbrush of claim 1 wherein said brush head carries bristles defining said brushing plane.

3. The toothbrush of claim 1 further comprising:

a drive mechanism having a rotary crank rotatably connected to said brush head such that in response to rotation of said rotary crank said brush head is moved along the endless path of revolution.

4. The toothbrush of claim 3 wherein said brush head includes:

a head portion carrying bristles which define said brushing plane; and a plate portion rotatably supporting said head portion such that said head portion is capable of undergoing rotation relative to said plate portion as both said head and plate portions undergo movement along the endless path of revolution.

5. The toothbrush of claim 4 further comprising:

a linkage pivotally connected to said handle and said head and plate portions of said brush head such that said head portion in response to rotation of said rotary crank is caused to rotate relative to said plate portion and move along an oscillatory path as said head and plate portions of said brush head are moved together along the endless path of revolution.

6. The toothbrush of claim 1 wherein said guide arrangement further includes forward and rearward slide rods spaced apart and extending transversely to said respective forward and rearward pairs of said guide posts and between and attached to said sleeves on said pairs of guide posts.

7. The toothbrush of claim 6 wherein said brush head is slidably supported on said slide rods so as to be capable of concurrently undergoing horizontal movement along said slide rods toward and away from said guide posts and sleeves and vertical movement with said slide rods and sleeves along said guide posts and thereby revolving movement about the endless path of revolution.

8. The toothbrush of claim 7 further comprising:

a drive mechanism having a rotary crank rotatably connected to said brush head such that in response to rotation of said rotary crank said brush head is moved along the endless path of revolution.

\* \* \* \* \*